US009950153B2

(12) United States Patent
Wagner et al.

(10) Patent No.: US 9,950,153 B2
(45) Date of Patent: *Apr. 24, 2018

(54) INTERFACE APPARATUS FOR STIMULATION OF BIOLOGICAL TISSUE

(71) Applicant: Highland Instruments, Inc., Somerville, MA (US)

(72) Inventors: Timothy Andrew Wagner, Somerville, MA (US); Uri Tzvi Eden, Somerville, MA (US)

(73) Assignee: Highland Instruments, Inc., Somerville, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/520,738

(22) Filed: Oct. 22, 2014

(65) Prior Publication Data
US 2015/0039055 A1 Feb. 5, 2015

Related U.S. Application Data

(63) Continuation of application No. 14/257,467, filed on Apr. 21, 2014, now Pat. No. 8,977,354, which is a (Continued)

(51) Int. Cl.
*A61N 1/04* (2006.01)
*A61N 1/36* (2006.01)
(Continued)

(52) U.S. Cl.
CPC ......... *A61N 1/0484* (2013.01); *A61N 1/0408* (2013.01); *A61N 1/0452* (2013.01);
(Continued)

(58) Field of Classification Search
CPC .... A61N 1/36025; A61N 7/00; A61N 1/0408; A61N 1/0452; A61N 1/0472;
(Continued)

(56) References Cited

U.S. PATENT DOCUMENTS 2,830,578 A 4/1958 Degroff et al.
2,838,672 A 6/1958 Leah et al.
(Continued)

OTHER PUBLICATIONS

Montalibet, A., et al., Electric current generated by ultrasonically induced Lorentz force in biological media. Med. Biol. Eng. Comput., 2001, vol. 39, pp. 15-20.
(Continued)

*Primary Examiner* — Mark W Bockelman
(74) *Attorney, Agent, or Firm* — Brown Rudnick LLP

(57) ABSTRACT

An apparatus for interfacing between tissues being stimulated is provided. The apparatus includes an electric source capable of generating an applied electric field across a region of tissue and/or a means for altering at least one electromagnetic characteristic of the region of tissue relative to the applied electric field and an interface component, such interface component creating an interface between the region of tissue and the applied electric field or the means for altering at least one electromagnetic characteristic of the region of tissue.

9 Claims, 3 Drawing Sheets

Related U.S. Application Data continuation of application No. 12/536,914, filed on Aug. 6, 2009, now Pat. No. 8,718,758, which is a continuation-in-part of application No. 11/764,468, filed on Jun. 18, 2007, now Pat. No. 8,929,979.

(60) Provisional application No. 61/086,989, filed on Aug. 7, 2008, provisional application No. 60/814,843, filed on Jun. 19, 2006.

(51) Int. Cl.
*A61N 1/40* (2006.01)
*A61N 7/00* (2006.01)

(52) U.S. Cl.
CPC ....... *A61N 1/0472* (2013.01); *A61N 1/36014* (2013.01); *A61N 1/36025* (2013.01); *A61N 1/40* (2013.01); *A61N 7/00* (2013.01); *A61N 1/0456* (2013.01)

(58) Field of Classification Search
CPC .............. A61N 1/36014; A61N 1/0456; A61N 1/0484; A61N 1/40
USPC .................................. 607/3, 45, 139; 601/2
See application file for complete search history.

(56) References Cited

U.S. PATENT DOCUMENTS

| | | | |
|---|---|---|---|
| 3,735,756 A | 5/1973 | Richards et al. | |
| 3,822,708 A | 7/1974 | Zilber | |
| 4,207,904 A * | 6/1980 | Greene | A61N 1/0492 607/152 |
| 4,305,402 A | 12/1981 | Katims | |
| 4,503,863 A | 3/1985 | Katims | |
| 4,535,785 A | 8/1985 | van den Honert et al. | |
| 4,611,596 A | 9/1986 | Wasserman | |
| 4,641,633 A | 2/1987 | Delgado | |
| 4,672,951 A | 6/1987 | Welch | |
| 4,690,144 A * | 9/1987 | Rise | A61N 1/36014 607/59 |
| 4,723,536 A | 2/1988 | Rauscher et al. | |
| 4,759,377 A | 7/1988 | Dykstra | |
| 4,805,636 A | 2/1989 | Barry et al. | |
| 4,889,526 A | 12/1989 | Rauscher et al. | |
| 4,923,437 A | 5/1990 | Gordon | |
| 5,014,699 A | 5/1991 | Pollack et al. | |
| 5,061,234 A | 10/1991 | Chaney | |
| 5,113,859 A | 5/1992 | Funke | |
| 5,205,297 A * | 4/1993 | Montecalvo et al. | 607/152 |
| 5,277,694 A | 1/1994 | Leysieffer et al. | |
| 5,300,093 A | 4/1994 | Koestner et al. | |
| 5,545,124 A | 8/1996 | Krause et al. | |
| 5,551,953 A * | 9/1996 | Lattin et al. | 604/20 |
| 5,569,591 A | 10/1996 | Kell et al. | |
| 5,575,761 A | 11/1996 | Hajianpour | |
| 5,713,922 A | 2/1998 | King | |
| 5,776,170 A | 7/1998 | MacDonald et al. | |
| 5,776,171 A | 7/1998 | Peckham et al. | |
| 5,893,883 A | 4/1999 | Torgerson et al. | |
| 5,904,712 A * | 5/1999 | Axelgaard | 607/148 |
| 5,925,070 A | 7/1999 | King et al. | |
| 5,975,085 A | 11/1999 | Rise | |
| 6,035,236 A | 3/2000 | Jarding et al. | |
| 6,081,744 A | 6/2000 | Loos | |
| 6,091,992 A | 7/2000 | Bourgeois et al. | |
| 6,094,598 A | 7/2000 | Elsberry et al. | |
| 6,102,875 A | 8/2000 | Jones | |
| 6,128,537 A | 10/2000 | Rise | |
| 6,161,048 A | 12/2000 | Sluijter et al. | |
| 6,169,403 B1 | 1/2001 | Hebrank et al. | |
| 6,205,356 B1 | 3/2001 | Holcomb | |
| 6,231,604 B1 | 5/2001 | von Ilberg | |
| 6,275,735 B1 | 8/2001 | Jarding et al. | |
| 6,275,737 B1 | 8/2001 | Mann | |
| 7,771,341 B2 * | 8/2010 | Rogers | 600/9 |
| 2004/0236268 A1 * | 11/2004 | Mitragotri et al. | 604/20 |
| 2006/0173510 A1 * | 8/2006 | Besio et al. | 607/45 |
| 2008/0171953 A1 * | 7/2008 | Mische | A61H 23/02 601/2 |
| 2009/0099623 A1 * | 4/2009 | Bentwich | A61N 1/36025 607/45 |

OTHER PUBLICATIONS

Mouchawar, G., et al., Magnetic Stimulation of excitable tissue: calculation of induced eddy currents with a three-dimensional finite-element model. IEEE Transactions on Magnetics, 1993. 29(6): p. 3355-3357.

Murasugi, C.M., C.D. Salzman, and W.T. Newsome, Microstimulation in visual area MT: effects of varying pulse amplitude and frequency. J Neurosci, 1993. 13(4): p. 1719-29.

Mushahwar, V.K. and K.W. Horch, Selective activation of muscle groups in the feline hindlimb through electrical microstimulation of the ventral lumbo-sacral spinal cord. IEEE Trans Rehabil Eng, 2000. 8(1): p. 11-21.

Nadeem, M., et al., Computation of electric and magnetic stimulation in human head using the 3-D impedance method. IEEE Transactions on Biomedical Engineering, 2003. 50(7): p. 900-907.

Nagarajan, S. and D.M. Durand, Analysis of magnetic stimulation of a concentric axon in a nerve bundle. IEEE Transactions on Biomedical Engineering, 1995. 42(9): p. 926-933.

Nagarajan, S., D.M. Durand, and E.N. Warman, Effects of induced electric fields on finite neuronal structures: a simulation study. IEEE Transactions on Biomedical Engineering, 1993. 40(11): p. 1175-1188.

Nagarajan, S., et al. Magnetic stimulation of finite neuronal structures. in Annual International Conference of the IEEE Engineering in Medicine and Biology Society. 1991: IEEE.

Nathan, S.S., et al., Determination of current density distributions generated by electrical stimulation of the human cerebral cortex. Electroencephalogr Clin Neurophysiol, 1993. 86(3): p. 183-92.

Neri Accornero et al., 'Visual evoked potentials modulation during direct current cortical polarization', Experimental Brain Research, Oct. 19, 2006, vol. 178, No. 2, pp. 261-266.

Nichols, M.J. and W.T. Newsome, Middle temporal visual area microstimulation influences veridical judgments of motion direction. J Neurosci, 2002. 22(21): p. 9530-40.

NorthstarNeuorsciences, Northstar Neuroscience Announces Primary Endpoint Results of EVEREST Clinical Trial. 2008: Seattle. p. 1.

Norton, 2003, Can ultrasound be used to stimulate nerve tissue, BioMedical Engineering OnLine 2(6):1-9.

O'Brien, W.D., Jr., Ultrasound-biophysics mechanisms. Prog Biophys Mol Biol, 2007. 93(1-3): p. 212-55.

Pascual-Leone, A., D. Bartres-Faz, and J.P. Keenan, Transcranial magnetic stimulation: studying the brain-behaviour relationship by induction of 'virtual lesions'. Philos Trans R Soc Lond B Biol Sci, 1999. 354(1387): p. 1229-38.

Perlmutter, J.S. and J.W. Mink, Deep Brain Stimulation. Annu Rev Neurosci, 2006.

Pernot, M., et al., In vivo transcranial brain surgery with an ultrasonic time reversal mirror. J Neurosurg, 2007. 106(6): p. 1061-6.

Plonsey R, Heppner DB (1967) Considerations of quasi-stationarity in electrophysiological systems. Bull Math Biophys 29:657-664.

Priori, A., Brain polarization in humans: a reappraisal of an old tool for prolonged non-invasive modulation of brain excitability. Clin Neurophysiol, 2003. 114(4): p. 589-95.

Prochazka, A., V.K. Mushahwar, and D.B. McCreery, Neural prostheses. J Physiol, 2001. 533(Pt 1): p. 99-109.

Purpura, D.P. and J.G. McMurtry, Intracellular Activities and Evoked Potential Changes During Polarization of Motor Cortex. J Neurophysiol, 1965. 28: p. 166-85.

Ramos-Estebanez, C., et al., Visual phosphene perception modulated by subthreshold crossmodal sensory stimulation. J Neurosci, 2007. 27(15): p. 4178-81.

(56) References Cited

OTHER PUBLICATIONS

Ranck, J.B., Jr., Which elements are excited in electrical stimulation of mammalian central nervous system: a review. Brain Res, 1975. 98(3): p. 417-40.
Rattay, F., et al., Mechanisms of Electrical Stimulation with Neural Prostheses. Neuromodulation, 2003. 6(1): p. 42-56.
Rezai, A.R., et al., Deep brain stimulation for Parkinson's disease: surgical issues. Mov Disord, 2006. 21 Suppl 14: p. S197-218.
Romo, R., et al., Somatosensory discrimination based on cortical microstimulation. Nature, 1998. 392(6674): p. 387-90.
Roth, B.J., Mechanisms for electrical stimulation of excitable tissue. Critical Reviews in Biomedical Engineering, 1994. 22(3-4): p. 253-305.
Rousche, P. and R. Normann, Chronic Intracortical Microstimulation (ICMS) of Cat Sensory Cortex Using the Utah Intracortical Electrode Array. IEEE Trans Rehabil Eng, 1999. 7(1): p. 56-68.
Rush, S. and D.A. Driscoll, Current distribution in the brain from surface electrodes. Anesth Analg, 1968. 47(6): p. 717-23.
Rutten, W.L.C., et al., The influence of ultrasound and ultrasonic focusing on magnetic and electric peripheral nerve stimulation., in Advances in Magnetic Stimulation: Mathematical modeling and clinical applications, J. Nilsson, M. Panizza, and F. Grandori, Editors. 1996: Pavia, Italy. p. 152.
Salzman, C.D., et al., Microstimulation in visual area MT: effects on direction discrimination performance. J Neurosci, 1992. 12(6): p. 2331-55.
Salzman, C.D., K.H. Britten, and W.T. Newsome, Cortical microstimulation influences perceptual judgements of motion direction. Nature, 1990. 346(6280): p. 174-7.
Saypol, J.M., et al., A theoretical comparison of electric and magnetic stimulation of the brain. Annals of Biomedical Engineering, 1991. 19(3): p. 317-28.
Tranchina, D. and C. Nicholson, A model for the polarization of neurons by extrinsically applied electric fields. Biophys J, 1986. 50(6): p. 1139-56.
Traub RD (1977) Motorneurons of different geometry and the size principle. Biol Cybern 25:163-176.
Troster, A.I., et al., Neuropsychological deficits in essential tremor: an expression of cerebello-thalamo-cortical pathophysiology? Eur J Neurol, 2002. 9(2): p. 143-51.
Tyler, W.J., et al., Remote excitation of neuronal circuits using low-intensity, low-frequency ultrasound. PLoS One, 2008. 3(10): p. e3511.
Ueno, S., T. Tashiro, and K. Harada, Localised stimulation of neural tissues in the brain by means of a paired configuration of time-varying magnetic fields. J. Appl. Phys., 1988. 64: p. 5862-5864.
Wagner T, Valero-Cabre A, Pascual-Leone A (2007) Noninvasive Human Brain Stimulation. Annu Rev Biomed Eng.
Wagner TA, Zahn M, Grodzinsky AJ, Pascual-Leone A (2004) Three-dimensional head model simulation of transcranial magnetic stimulation. IEEE Trans Biomed Eng 51:1586-1598.
Wagner, T., et al., Biophysical foundations underlying TMS: Setting the stage for an effective use of neurostimulation in the cognitive neurosciences. Cortex, 2008.
Wagner, T., et al., Transcranial direct current stimulation: a computer-based human model study. Neuroimage, 2007. 35(3): p. 1113-24.
Wagner, T., et al., Transcranial magnetic stimulation and brain atrophy: a computer-based human brain model study. Exp Brain Res, 2008.
Wagner, T., et al., Transcranial magnetic stimulation and stroke: a computer-based human model study. Neuroimage, 2006. 30(3): p. 857-70.
Wagner, T., Field distributions within the human cortex induced by transcranial magnetic stimulation, in EECS. 2001, Massachusetts Institute of Technology: Cambridge. p. 186.
Warman, E.N., W.M. Grill, and D. Durand, Modeling the effects of electric fields on nerve fibers: determination of excitation thresholds. IEEE Trans Biomed Eng, 1992. 39(12): p. 1244-54.
Wichmann, T. and M.R. Delong, Deep brain stimulation for neurologic and neuropsychiatric disorders. Neuron, 2006. 52(1): p. 197-204.
Wininger, F.A., J.L. Schei, and D.M. Rector, Complete optical neurophysiology: toward optical stimulation and recording of neural tissue. Appl Opt, 2009. 48(10): p. D218-24.
Wobschall, D., Bilayer Membrane Elasticity and Dynamic Response. Journal of Colloid and Interface Science, 1971. 36(3): p. 385-396.
Wobschall, D., Voltage Dependence of Bilayer Membrane Capacitance. Journal of Colloid and Interface Science, 1972. 40(3): p. 417-423.
Wongsarnpigoon, A. and W.M. Grill, Computational modeling of epidural cortical stimulation. J Neural Eng, 2008. 5(4): p. 443-54.
Zangen, A., et al., Transcranial magnetic stimulation of deep brain regions: evidence for efficacy of the H-coil. Clin Neurophysiol, 2005. 116(4): p. 775-9.
Gielen, F. Deep Brain Stimulation: Current Practice and Challenges for the Future. in 1st International IEEE EMBS Conference on Neural Engineering. 2003. Capri Island, Italy: IEEE.
Graziano, M.S., C.S. Taylor, and T. Moore, Complex movements evoked by microstimulation of precentral cortex. Neuron, 2002. 34(5): p. 841-51.
Grill, W.M., et al., Temporal excitation properties of paresthesias evoked by thalamic microstimulation. Clin Neurophysiol, 2005. 116(5): p. 1227-34.
Grill, W.M., S.E. Norman, and R.V. Bellamkonda, Implanted neural interfaces: biochallenges and engineered solutions. Annu Rev Biomed Eng, 2009. 11: p. 1-24.
Grosse, C., Permitivity of suspension of charged particles in electolyte solution. J. Chem. Phys., 1987. 91: p. 3073.
Gusev, V., et al., Imaging With the Ultrasonic Vibration Potential: A Theory for Current Generation. Ultrasound in Med. & Biol., 2005. vol. 31, No. 2, pp. 273-278.
Haar, G.t., Accoustic Surgery. Physics Today, 2001: p. 29-34.
Hart FX, Toll RB, Berner NJ, Bennett NH (1996) The low frequency dielectric properties of octopus arm muscle measured in vivo. Phys Med Biol 41:2043-2052.
Hart, F.X. and W.R. Dunfree, In vivo measurements of low frequency dielectric spectra of a frog skeletal muscle. Phys. Med. Biol., 1993. 38: p. 1099-1112.
Hatanaka, N., et al., Input-output organization of jaw movement-related areas in monkey frontal cortex. J Comp Neurol, 2005. 492(4): p. 401-25.
Heller L, Hulsteyn DBv (1992) Brain stimulation using electromagnetic sources: theoretical aspects. Biophysical Journal 63:129-138.
Hinch, E.J., et al., Dielectric response of a dilute suspension of spheres with thin double layers in an asymmetric electrolyte. J Chem Soc, Farady Tans., 1983. 80: p. 535-551.
Holdefer, R.N., R. Sadleir, and M.J. Russell, Predicted current densities in the brain during transcranial electrical stimulation. Clin Neurophysiol, 2006. 117(6): p. 1388-97.
Hole, S. and T. Ditchi, Non-destructive Methods for Space Charge Distribution Measurements: What are the Differences? IEEE EMBS, 2003. 10(4): p. 670-677.
Hsiao, I. and V. Lin, Improved coil design for functional magnetic stimulation of expiratory muscles. IEEE Trans Biomed Eng, 2001. 48(6): p. 684-694.
Hsu KH and D. DM., A 3-D differential coil design for localized magnetic stimulation. IEEE Trans Biomed Eng, 2001. 48(10): p. 1162-8.
International Search Report dated Mar. 18, 2010 (three pages).
Jones KE, Bawa P (1997) Computer simulation of the responses of human motoneurons to composite 1A EPSPS: effects of background firing rate. J Neurophysiol 77:405-420.
Kanai, R., et al., Frequency-dependent electrical stimulation of the visual cortex. Curr Biol, 2008. 18(23): p. 1839-43.
Kanner, A.M., Deep brain stimulation for intractable epilepsy: which target and for which seizures? Epilepsy Curr, 2004. 4(6): p. 231-2.
Kaufman, E.F. and A.C. Rosenquist, Efferent projections of the thalamic intralaminar nuclei in the cat. Brain Res, 1985. 335(2): p. 257-79.

(56) References Cited

OTHER PUBLICATIONS

Khachaturian, M.H., et al., Focal reversible deactivation of cerebral metabolism affects water diffusion. Magn Reson Med, 2008. 60(5): p. 1178-89.

Khraiche, M.L., et al., Ultrasound induced increase in excitability of single neurons. Conf Proc IEEE Eng Med Biol Soc, 2008. 2008: p. 4246-9.

Kleim, J.A., T.A. Jones, and T. Schallert, Motor enrichment and the induction of plasticity before or after brain injury. Neurochem Res, 2003. 28(11): p. 1757-69.

Komissarow, L., et al., Triple stimulation technique (TST) in amyotrophic lateral sclerosis. Clin Neurophysiol, 2004. 115(2): p. 356-60.

Kraus, K.H., et al., The use of a cap-shaped coil for transcranial magnetic stimulation of the motor cortex. J Clin Neurophysiol, 1993. 10(3): p. 353-62.

Kumar, K., C. Toth, and R.K. Nath, Deep brain stimulation for intractable pain: a 15-year experience. Neurosurgery, 1997. 40(4): p. 736-46; discussion 746-7.

Larkin, J., et al., Combined electric field and ultrasound therapy as a novel anti-tumour treatment. European Journal of Cancer 41 (2005) 1339-1348.

Lemay, M.A., et al. Endpoint forces obtained during intraspinal microstimulation of the cat lumbar spinal cord—experimental and biomechanical model results. In IEEE 28th Annual Northeast Bioengineering Conference, 2002. 2002: IEEE.

Li, D.L., et al., Finite element analysis of transcranial electrical stimulation for intraoperative monitoring. in Bioengineering Conference, 2005. Proceedings of the IEEE 31st Annual Northeast 2005: IEEE.

Lin, V., I. Hsiao, and V. Dhaka, Magnetic coil design considerations for functional magnetic stimulation. IEEE Trans Biomed Eng, 2000. 47(5): p. 600-610.

Lomber, S.G., The advantages and limitations of permanent or reversible deactivation techniques in the assessment of neural function. J Neurosci Methods, 1999. 86(2): p. 109-17.

Lozano, A.M., et al., Deep brain stimulation for Parkinson's disease: disrupting the disruption. Lancet Neurol, 2002. 1(4): p. 225-31.

\* cited by examiner

INTERFACE APPARATUS FOR STIMULATION OF BIOLOGICAL TISSUE

CROSS-REFERENCE TO RELATED APPLICATIONS

This patent application is a continuation of U.S. application Ser. No. 14/257,467, filed in the U.S. Patent and Trademark Office on Apr. 21, 2014, which is a continuation of U.S. application Ser. No. 12/536,914 filed in the U.S. Patent and Trademark Office on Jun. 18, 2009, which claims priority to U.S. Provisional Application Ser. No. 61/086,989 filed in the U.S. patent and Trademark Office on Aug. 7, 2008 by Wagner, and is a continuation-in-part of U.S. application Ser. No. 11/764,468, filed in the U.S. Patent and Trademark Office on Jun. 18, 2007 by Wagner et al., which claims priority to U.S. Provisional Application Ser. No. 60/814,843 filed in the U.S. patent and Trademark Office on Jun. 19, 2006, the entire contents of each of which are incorporated herein by reference in their entirety.

I. BACKGROUND OF THE INVENTION

A. Field of the Invention

The present disclosure relates generally to the field of altering and/or generating currents in biological tissue for the purpose of stimulation. More particularly, the present disclosure relates to an apparatus that serves as an interface mechanism between tissue being stimulated and/or an electrical field (and/or electric field source) and/or a means for altering the tissue electromagnetic parameters (fields, agents, and/or sources).

B. Background Information

Electric stimulation of living tissue in humans and other animals is used in a number of clinical applications as well as in general biological research. In particular, electric stimulation of neural tissue has been used in the treatment of various diseases including Parkinson's disease, depression, and intractable pain. Focused and/or deep stimulation of the brain usually involves performing surgery to remove a portion of the skull and implanting electrodes in a specific location within the brain tissue. The invasive nature of these procedures makes them difficult and costly, and is responsible for a great deal of morbidity. Alternately, noninvasive stimulation methodologies such as transcranial direct current stimulation (tDCS) and transcranial magnetic stimulation (TMS) are easy to implement and are not associated with significant morbidity, however, the areas stimulated are large, typically not well characterized, and can be significantly perturbed by natural or pathological features of the brain tissue. Recently, ultrasound stimulation of brain tissue has been explored with limited success, as it alone does not generate currents that are the backbone of clinically effective stimulation methods.

Numerous methods exist for generating currents for biological tissue stimulation. These methods range from implanting electric sources in the tissue to inductively generating currents in tissue via time-varying magnetic fields. A new method for generating currents in biological tissue was recently described in U.S. patent application Ser. No. 11/764,468, Apparatus and Method for Stimulation of Biological Tissue, which discloses an apparatus and method of generating currents in biological tissues. The disclosure describes a means to stimulate biological tissue via an electric source capable of generating an electric field across a region of tissue and a means for altering the electromagnetic properties of tissue relative to the electric field, whereby the alteration of the tissue electromagnetic properties relative to the electric field generates an altered current in the tissue. These alterations in the current in turn lead to the stimulation of biological tissue. The means for altering these electromagnetic parameters of the tissue could include a chemical, optical, mechanical, thermal, and/or secondary electromagnetic source(s), field(s), and/or agents.

Presently, no apparatus exists which can improve on the interface between the primary electric source (and/or field) and/or means to alter tissue electromagnetic properties (source(s), field(s), and/or agents) and/or the tissue(s) to be stimulated for this type of tissue stimulation method. No interface exists which can regulate the number of and/or duration of stimulation sessions. No interface exists which can control, move, and/or fix the location and/or sizes of the source of the primary electric field and/or means for altering the electromagnetic properties of the tissue(s) to be stimulated for this type of tissue stimulation method. No interface exists Which specifically bridges, couples, and/or matches the properties of the materials between the primary electrical field source (and/or its field) and/or the source of the means for altering these electromagnetic parameters of the tissue (and/or the fields and/or agents) and/or the tissue in such a way to improve stimulation for this type of tissue stimulation method. No interface has been proposed which can be worn, integrated with wearable items, house any of the sources of stimulation, and/or serve as a bridge between tissue(s) to be stimulated and any of the sources of stimulation.

It would be desirable to provide an interface mechanism between the stimulated tissue and/or the source electrical field(s) and/or the means for altering the tissue's electromagnetic characteristics that makes such improvements. The present disclosure addresses these deficiencies.

II. SUMMARY OF THE INVENTION

Accordingly, an interface apparatus is presented. The interface apparatus could be used to regulate the number of stimulation sessions (and/or duration of stimulation), house the electrical field source and/or the source of the means for altering the tissue's electromagnetic characteristics, and/or act as a bridging medium between the tissue and/or the electric field (and/or source) and/or the means for altering the tissues electromagnetic properties (source(s), field(s), and/or agents). The interface apparatus according to the present disclosure can include an electric source capable of generating an applied electric field across a region of tissue, a means for altering at least one electromagnetic characteristic of the region of tissue relative to the applied electric field, and an interface component, such interface component creating an interface between the region of tissue and applied electric field and/or the means for altering at least one electromagnetic characteristic of the region of tissue. It is envisioned that according to the present disclosure, the characteristics of tissue can be altered using a variety of sources including, but not limited to, a chemical source, optical source, mechanical source, thermal source, and/or a secondary electromagnetic source (and/or the source generated field(s) and/or agents).

According to the current disclosure, the tissue permittivity can be altered relative to an applied electric field. The alteration then generates a displacement current in the region of tissue. Further conductivity can be altered relative to an applied electric field thereby generating an altered ohmic current. The alteration of an electromagnetic characteristic of a region of tissue can also be used to generate a new electric field that has the ability to drive additional ohmic and displacement currents.

The interface apparatus can include either a separate piece that is a wearable component (such as for example a helmet that could be worn by the person being stimulated in the brain); an external wrap(s) (of various shapes tailored for any part of the body) or wearable items; bridging blocks; electrode like components; transducer like components; materials that can be worn and/or integrated into other wearable items; a physical boundary component of the headpiece of a transducer mechanism for the field(s) and/or electromagnetic tissue parameter(s) modifier(s); any physical boundary component which directs or couples at least one of the sources, fields, agents, or means for altering tissue electromagnetic properties with the tissue; and/or any combination of the above.

The interface apparatus may have its number of uses regulated (and/or the duration of stimulation) through multiple methods including use of an integrated electrical circuit, which can control the number of uses (or time) through which the interface component may be used (which may be controlled for example through electrical or mechanical interfaces, memory devices, card readers, telecommunication devices, etc); use of interface creams, pastes, fluids, materials, and/or gels which can be fashioned to be only functional for a single use (or a controlled number of uses and/or duration of stimulation); use of mechanical safety latches which deactivates the item after a single use (or a controlled number of uses and/or duration of stimulation); and/or use of a composite material which makes up part of the apparatus according to the present disclosure and can regulate the number of applications and/or duration of stimulation; and/or other standard mechanisms (all used individually or in any combination).

The interface apparatus according to the present disclosure could be used to match and/or appropriately couple the physical characteristics between the tissue(s) and/or the electrical field (or electric field source) and/or means for altering the tissue electromagnetic parameters to augment, focus, modify, and/or improve the current alteration. The interface could also be used to adjust the position, shape, and/or size of the components of the stimulation method that can be housed in the interface and/or in contact with the interface relative to the tissue to be stimulated.

III. BRIEF DESCRIPTION OF THE DRAWINGS

The above-mentioned and other features and objects of this invention, and the manner of attaining them, will become more apparent and the invention itself will be better understood by reference to the following description of embodiments of the invention taken in conjunction with the accompanying drawings, wherein.

IV. DETAILED DESCRIPTION OF EMBODIMENTS OF THE INVENTION

Figure 1:
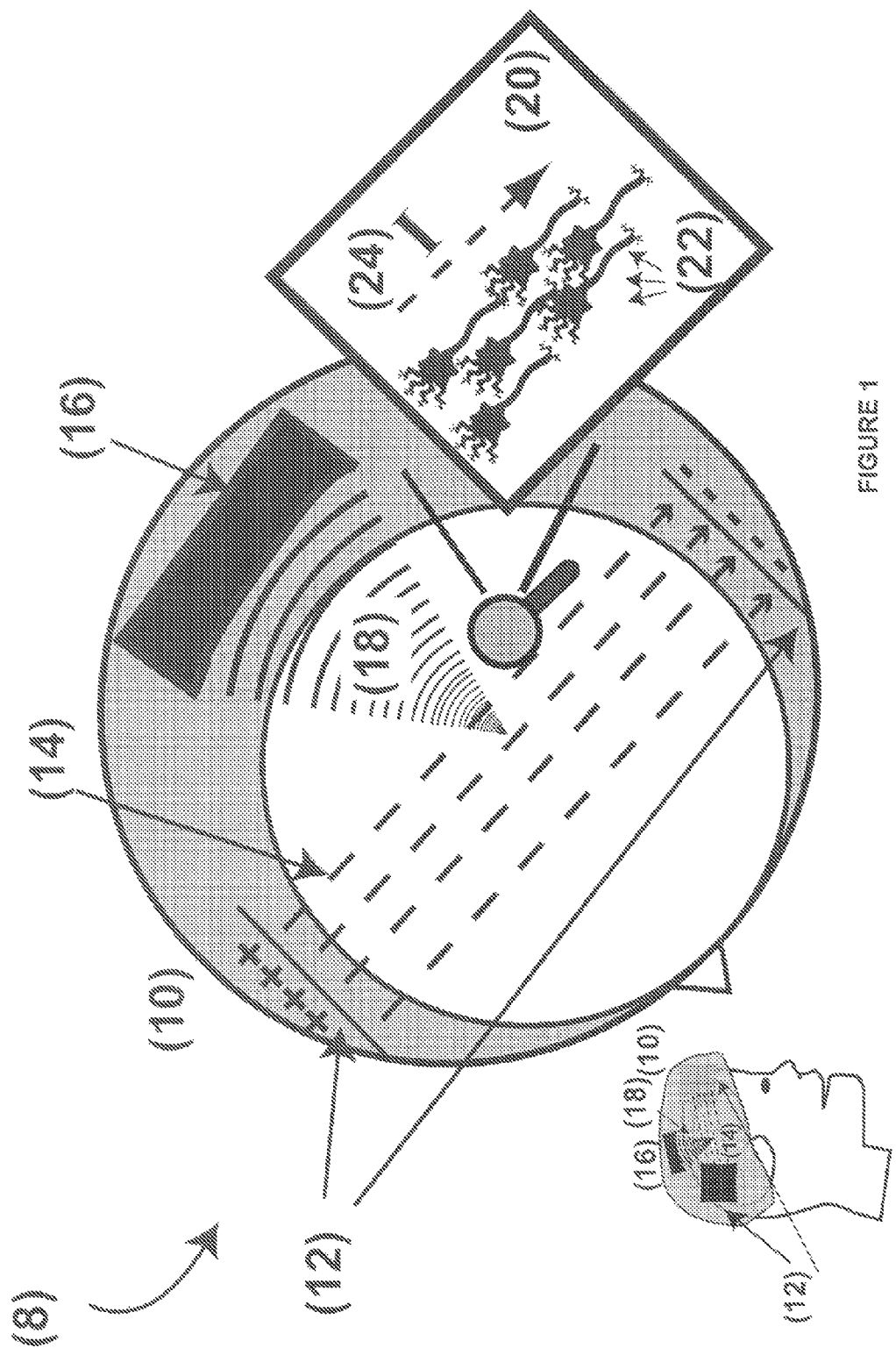
FIG. 1 is a plan view of an exemplary embodiment of an interface apparatus in accordance with the present disclosure.

It is envisioned that the present disclosure may be used as a method to augment or use in connection with the stimulation of biological tissue through the methods described in U.S. patent application Ser. No. 11/764,468, Apparatus and Method for Stimulation of Biological Tissue, where an electric source that is placed on the body to generate an electric field is combined with a means for altering the electromagnetic properties of the tissue relative to the electric field, whereby the alteration of the tissue electromagnetic properties relative to the electric field generates an altered current in the tissues.

As provided by the present disclosure, an interface apparatus is introduced. The interface apparatus according to the present disclosure can be used between stimulated tissue and/or the primary electric field (or electric field source) and/or the means for altering the electromagnetic tissue parameters (i.e., the ultrasound/mechanical field and/or source(s), chemical agent and/or source(s), thermal field and/or source(s), optical field/beam and/or source(s), and/or secondary electromagnetic field and/or source(s)). The exemplary embodiments of the apparatus disclosed can be employed in the area of neural stimulation and muscular stimulation (including cardiac stimulation). It is also envisioned that the present disclosure may also be employed in the area of cellular metabolism, physical therapy, drug delivery, and gene therapy.

A detailed embodiment of the present disclosure is presented herein, however, it is to be understood that the described embodiments are merely exemplary of the disclosure, which may be embodied in various forms. Therefore, specific functional details disclosed herein are not to be interpreted as limiting, but merely as a basis for the claims and as a representative basis for teaching one skilled in the art to variously employ the present disclosure in virtually any appropriately detailed embodiment.

The components of the tissue stimulation interface apparatus according to the present disclosure are fabricated from materials suitable for a variety of medical applications, such as, for example, polymerics, gels, films, fabrics, and/or metals, depending on the particular application and/or preference. Semi-rigid and rigid polymerics are contemplated for fabrication, as well as resilient materials, such as molded medical grade polyurethane, as well as flexible or malleable materials, such as fabrics, flexible polymerics, or materials for wearable items. The motors, gearing, electronics, power components, electrodes, and transducers of the apparatus may be fabricated from those suitable for a variety of medical applications. The interface apparatus according to the present disclosure may also be used in connection with or include circuit boards, circuitry, processor components, etc. for computerized control. One skilled in the art, however, will realize that other materials and fabrication methods suitable for assembly and manufacture, in accordance with the present disclosure, also would be appropriate.

The following discussion includes a description of the components and exemplary methods for creating an interface between tissue and/or an electric field (and/or electric field source) and/or means for altering the electromagnetic tissue parameters (source(s), field(s), and/or agents). Reference will now be made in detail to the exemplary embodiments of the present disclosure illustrated in the accompanying figure wherein like reference numerals indicate the similar parts throughout the figure.

Turning now to FIG. 1, which illustrates an exemplary embodiment of an interface apparatus 8. An interface component 10 can be used to provide an interface between the tissue, and the electric field (and source), and means for altering the electromagnetic tissue properties. For example, the interface apparatus 8 illustrated in FIG. 1 according to the present disclosure may be applied to the area of neural stimulation (and in particular brain stimulation).

Electrodes 12, as an electric source, are applied to the scalp through interface component 10. As depicted in FIG. 1, interface component 10, can be a cap, helmet, or other item that can be worn by an individual. Further, it is envisioned that electrodes 12 can be separate or attached to, embedded in, placed on top of, placed on the surface of or fastened within (or any combination to) the interface component 10. The cap interface component 10 can serve as an interface between regions of tissue of an individual and electrodes (or as a holder for the electrodes directly affixed to the skin with an area opened on the interface mechanism). While electrodes 12 are used and applied to the scalp through the interface mechanism in this exemplary embodiment, it is envisioned that the electrodes may be applied to a number of different areas on, within, or near the body including areas around the scalp through a single interface component, multiple interface components, and/or a combination of an interface component(s). The electrodes used may or may not be housed in an interface component of the interface apparatus according to the present disclosure. By way of example, the main electrode(s) used could be housed within an interface component affixed to the scalp and a free electrode could be placed in the subject's mouth. It is also envisioned that one electrode may be placed proximal to the tissue being stimulated and the other distant, such as one electrode on the scalp and one on the thorax (through a single interface component (containing at least one of the electrode elements, where the other electrodes may be housed in an interface component and/or as separate non-interface component-contained electrodes), and/or through multiple interface components).

It is further envisioned that the electric source could be mono-polar with a single electrode (where a cap interface component could serve as the entire or part of the electrode), or multi-polar with multiple electrodes where at least one of the electrodes is contained (or part of) in at least one interface component. Similarly, the electric source of the interface apparatus (and/or the interface component) may be applied to tissue via any medically acceptable medium (i.e., gels, creams, pastes, fluids, dry application electrodes, etc). By using dry electrodes (and/or a dry interface component), one could potentially eliminate the debris left on the subject following stimulation. It is also envisioned that the electric source could generate its field via inductive means whereby a magnetic source is embedded in the cap interface component. The interface component can itself be comprised of inert and/or active materials that serve as a bridging medium and appropriately couple and/or match the electromagnetic characteristics between an electrical source and a region or regions of tissue (for example, by actively or passively altering and/or matching the electrical impedances between the tissues and the electric source(s)). Finally the interface component(s) themselves(s) may serve as an electric source(s) itself, in whole or part.

The electrodes generate a source electric field 14, which results in a current in the tissue. As described in further detail below, the electromagnetic properties of the tissue are altered relative to the electric field, for example by a mechanical field, thereby generating a new and altered current component relative to the initial field and/or an additional new electrical field component, including ohmic and/or displacement current components.

As further depicted in FIG. 1, a mechanical source (the mechanical source may be any acoustic source such as an ultrasound device) 16 is applied on the scalp via interface mechanism 10 and provides concentrated acoustic energy 18 (i.e., mechanical field) to a focused region of neural tissue in the brain of a subject. This mechanical field 18 affects a smaller number of neurons 22 than is affected by the electric field 14 and thereby generates the altered current 24. A block of tissue 20, is depicted in a magnified view with neurons 22 to be stimulated in FIG. 1.

The mechanical source 16 and subsequent field 18 can be applied to the scalp through the interface mechanism 10, which can be a cap, helmet, or wearable item as depicted in FIG. 1. It is envisioned that the mechanical source can be attached to, embedded in, placed on top of, placed on the surface of, or fastened within (or any combination to) the interface component 10 of interface apparatus 8. Thus, the interface component 10 can serve as an interface between the region of tissue or tissues and mechanical source (or as a holder for the mechanical source in direct contact with the tissue). Multiple mechanical sources could be applied (through either one interface mechanism (with multiple mechanical sources), multiple interface mechanisms (containing or interfacing with at least one mechanical source), or through any such combination (and/or with separate non-interface component-contained mechanical sources)).

While a mechanical source 16 can be used and applied to the scalp through interface component 10 as depicted in this exemplary embodiment, it is envisioned that mechanical source(s) may be applied to a number of different areas on, within, or near the body including areas around the scalp through a single interface component, multiple interface components, and/or a combination of an interface component(s) and/or mechanical sources that are not housed in an interface component. Similarly, the mechanical source component of the interface apparatus (and/or the interface component) may be applied to tissue via any medically acceptable medium (i.e., gels, creams, fluids, pastes, etc). The interface component itself can be comprised of materials, active and/or inert, that serve as a bridging medium, thus creating the interface, and thereby appropriately coupling and/or matching the mechanical properties between the mechanical source and the targeted tissues (for example, by actively and/or passively matching and/or altering the acoustic impedances between the tissues and the electric source(s)). The interface component itself may serve as a mechanical source(s) itself, in whole or part.

As the electric field is to be coupled to the mechanical field, the interface component itself can be comprised of materials, active and/or inert, that serve as a bridging medium, thus creating an interface, and thereby appropriately couple and/or match the acoustic characteristics and/or electromagnetic properties between the mechanical source and/or fields (or other means for altering electromagnetic characteristics) and/or the electric source and/or fields and/or the tissues to augment the stimulation. This can be done for example, by having the interface component at least in part capable of: actively and/or passively matching and/or altering the electrical and acoustic impedances of the interface to the electrical and mechanical field frequencies that are tuned to initiate stimulation of neural cells, and/or actively and/or passively matching and/or altering the electrical and acoustic impedances of the interface to the sources such that the sources themselves are matched and more efficient in use, and/or altering its interface materials such that the speed of sound and/or light is changed in them so that the fields that impinge on the tissue to be stimulated are tuned to the nerve cells targeted, and/or altering the dispersive properties of its interface materials so the mechanical and/or electrical fields have a controllable frequency dependent behavior in the materials such as to tune the field frequencies to neural effect, and/or making its interface materials capable of filtering the fields as to tune the fields to neural effect, and/or altering the densities of the interface materials altering the transmission of fields through the interface to maximize neural effect, and/or allowing its interface materials to shift the phase of individual fields thereby restructuring the waveforms that impinge on the neural tissue, and/or altering the focus or targeting of the fields to stimulate different neural targets, and/or altering the orientation of the vector field components thereby potentially altering the neural response of the stimulated cell (for example inhibiting or facilitating the cells based on the final stimulating current density orientation relative to the neural body-axon axis), and/or altering the magnitude of the fields to maximize neural effect, and/or altering the field waveform dynamics/shapes to tune neural response, etc.

While a mechanical source 16 can be used and applied to the scalp through the interface mechanism in this exemplary embodiment, many other means could be applied to alter the electromagnetic properties of the underlying tissue, and similar property matching and/or coupling could be enacted across all of the different mechanisms for altering the electromagnetic properties of the tissue (including thermal, chemical, optical, electromagnetic, and/or mechanical properties) to generate the desired current for stimulation based on matching and/or coupling the source(s), field(s), and/or agent(s) and/or tissue properties through the interface.

It is further envisioned that the interface component may be comprised of one or separate pieces and serve only to couple the mechanical field with the underlying tissue or the electrical field with the underlying tissue separately (or they may be designed so that they are separate but integratable (or just used with separate non-housed electrical and/or mechanical sources)). The interface component(s) could also be designed to couple the electromagnetic and mechanical fields before being focused on the tissues, such as for example in an appropriate housing paradigm (potentially including the proper placement of the primary electric field source and the means for altering the electromagnetic tissue properties) whereby the fields are coupled appropriately before being focused on the tissues (or to facilitate the subsequent focusing on or into the tissues). The interface component(s) itself can be adjustable in shape, size and/or position, and/or allow for the movement and/or reshaping and/or resizing of the parts that are embedded within it or attached on it such that either of the sources (electrical and/or means for altering tissue characteristics) can be adjusted relative to the tissue to be stimulated (such as for example allowing movement of the electric field source or mechanical field source relative to the tissue as might be used for adjustable targeting of locations to be stimulated).

The interface apparatus(s) may have its number of uses controlled (and/or control the duration of a stimulation session(s)). This control could be used to increase the efficiency of its application or to avoid overuse. Examples in which uses could be controlled include incorporating an integrated electrical circuit which can control the number of uses (and/or stimulation session durations) through which the component may be used; using interface creams, fluids, materials, pastes, and/or gels which can be fashioned to be only functional for a single use (or a controlled number of uses and/or stimulation session duration); incorporating mechanical safety latches which deactivate the item after a single use (or a controlled number of uses and/or stimulation session duration); using a composite material which makes up part of the interface apparatus and can regulate the number of applications (and/or stimulation session duration); and/or other standard mechanisms (all used individually or in any combination). Additionally, the interface component(s) may be reusable, where the electrodes (i.e., electrical source components) and/or means for altering the tissue electromagnetic properties (i.e., ultrasound/mechanical, chemical, thermal, optical, and/or secondary electromagnetic source(s)) are removable and/or replaceable within the interface component and/or made of materials such that they are multi-use.

Other embodiments can incorporate item such as a separate piece(s) that are wearable component(s) for any Other body part including and beyond the head/scalp as mentioned above (such as a back brace like wearable items for spinal cord stimulation, a knee brace like component, etc), an external wrap(s) (of various shapes tailored for any part of the body), materials that can be worn separately and integrated into other wearable items, bridging blocks, electrode like components, a physical boundary component of the headpiece of a transducer mechanism for the primary electromagnetic field source and/or the means to modify the electromagnetic tissues parameters (that may serve as a medical device interface where the type of mechanism that facilitates the coupling of the fields could be used for a headpiece of a transducer of a medical device for applying the appropriate fields and/or additional means for altering the tissue electromagnetic parameters—this headpiece could for instance be integrated into chair type device that one might sit in for stimulation), and/or any combination of the above. Also, the different components could be made from multiple separate pieces, that may be integratable or separately functioning, such as for a cap like mechanism there could be one cap mechanism that serves to hold the electrical field source electrodes and a separate cap holding the ultrasound source (or sources of mechanical fields, chemical agents, thermal fields, optical fields/beams, and/or secondary electromagnetic fields), both made of materials to facilitate the transmission of the given fields and/or agents.

It is also envisioned that the interface component may be housing for materials, such as fluid(s) and/or gel(s), through which the mechanical energy and/or electrical energy transmits and/or materials at the transducer and/or electrode interface through which either or both fields transmit with underlying subject to be stimulated (for example an ultrasonic gel which also allows the conduction of electrical fields/currents). Thus, the interface component does not have to directly house either the electrical source or a means for altering the electromagnetic properties of tissue, but it can serve as an interface between tissues and an external electrical source and/or an external means for altering electromagnetic tissue properties which are adjacent to the interface (which could be matched and/or coupled in some way to the tissue to be stimulated (and/or to each other) through the interface apparatus). Thus, the interface apparatus could have neither the primary electric source nor the means to alter the electromagnetic properties of the tissue directly embedded within or attached to it, but could just serve to match and/or couple the properties of at least one of the components (together or individually and separately) and/or the tissue(s) to be stimulated through the proper matching and/or coupling of its material properties, inert and/or active, as exemplified above.

The interface component could also be implemented to augment stimulation in other ways. For example, the interface could be used to cool the tissue in the regions of the interface, for example if placed on the scalp the interface itself could maintain fluid which couples an ultrasound source to the scalp, but could be cooled at the same time such that the scalp and underlying skull itself do not heat due to ultrasound applications. Further, the nearby neural tissue can be cooled such that its metabolism is slowed at the surface allowing potentially more focal stimulation below (or to enact controlled stimulation at different regions of depth (for example where deeper tissues might not be cooled as much as the tissues proximal to the fluids, but in a way to help control the effects of neural stimulation)). Additionally, such cooling could be used to further alter the electromagnetic properties of the tissues.

Figure 2:
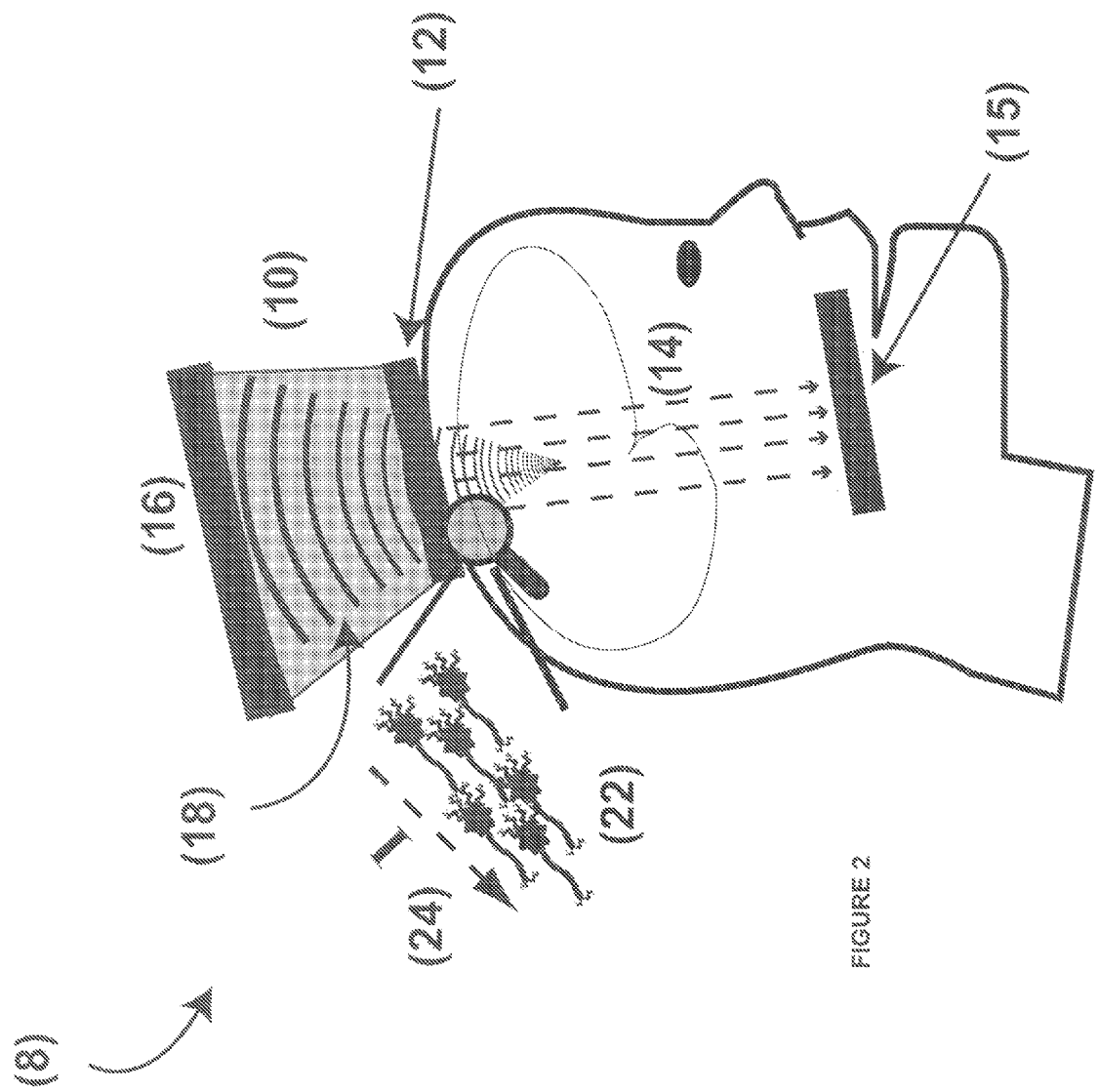
FIG. 2 is a plan view of an another exemplary embodiment of an interface apparatus in accordance with the present disclosure.

For all of the different combinations of means for altering the electromagnetic properties of the tissue and the primary electromagnetic source, the different source components (i.e., primary electrical source and/or mechanical, chemical, thermal, optical, and/or secondary electromagnetic source) can also be designed to allow the transmission of the fields (or agents, etc.) through each component if placed in such a way to be in one or another's transmission paths (an example of one such permutation is provided in the bridging block example of FIG. 2), where an externally applied ultrasound field can transmit through the primary electrical field source. On such example could be an apparatus where the electric field source could be designed of the appropriate acoustic properties such that it does not interfere with the transmission of the ultrasound field to the underlying tissues, or the electric field and mechanical field source are the same element(s)). It is envisioned that any permutation of placements is possible.

As previously mentioned, the means for altering the electromagnetic characteristics of tissue may be substituted or combined with any combination of mechanical fields, chemical agents, thermal fields, optical fields/beams, and/or secondary electromagnetic fields. The materials or properties of the interface component can be matched and/or coupled with the different sources and/or the primary electric field and/or the means to alter the tissue electromagnetic properties (source(s), field(s), and/or agent(s)) and/or the tissue to facilitate the current alteration process (with interface materials that are active and/or inert).

Thus, the interface apparatus according to the present disclosure could include a chemical source to alter at least one electromagnetic characteristic of the tissue(s) to be stimulated. In such a situation, it is envisioned that the interface component would comprise materials having appropriate properties such that a chemical reaction and/or a transmission of chemical agents between tissue and the chemical source is facilitated thereby creating an interface in part between tissue and the chemical source. It is also contemplated that an optical source can be used to alter at least one electromagnetic characteristics of tissue to be stimulated. The interface component could include materials having appropriate optical parameters such that the optical properties of the tissue(s), source(s), field(s), and/or the interface are matched and/or coupled thereby creating an interface in part between tissue and the optical source. Similarly, the means for altering at least one electromagnetic tissue characteristic of tissue(s) to be stimulated could be a thermal source. The interface component could include materials having appropriate thermodynamic parameters such that the thermodynamic properties of the tissue(s), source(s), field(s), and/or the interface are matched and/or coupled thereby creating an interface in part between tissue and the thermal source. Further, a secondary electromagnetic source could be used and the interface component could incorporate materials having appropriate electromagnetic parameters such that the electromagnetic characteristics between the tissue(s), source(s), field(s), and/or the interface are matched and/or coupled thereby creating an interface in part between said region of tissue and the electromagnetic source. And, the interface apparatus according to the present disclosure could include a mechanical (acoustic) source to alter at least one electromagnetic characteristic of the tissue(s) to be stimulated. In such a situation, it is envisioned that the interface component would comprise materials having appropriate mechanical (acoustic) properties such that the mechanical (acoustic) characteristics between the tissue(s), source(s), field(s), and/or the interface are matched and/or coupled thereby creating an interface in part between said region of tissue and the mechanical (acoustic) source. This concept of matching the properties may be applied in any permutation (via the interface and/or the tissues and/or with any potential sources, including the primary electrical source(s) and/or field and/or any means for altering the tissue electromagnetic properties (i.e., the ultrasound/mechanical field and/or source(s), chemical agent and/or source(s), thermal field and/or source(s), optical field/beam and/or source(s), and/or secondary electromagnetic field and/or source(s))).

FIG. 2, demonstrates an exemplary embodiment of the interface apparatus according to the present disclosure. For example, interface apparatus 8 illustrated in FIG. 2 according to the present disclosure may be applied to the area of neural stimulation (and in particular brain stimulation) and can serve as a bridging block interface mechanism between the sources and the tissue to be stimulated. An electrode 12, as an electric source, is applied to the scalp through the interface component 10, in which the electrode can be attached to, embedded in, placed on top of, or fastened within (or any combination to) the interface mechanism. The electrode 12 could be such that it is in direct contact with the tissue below, embedded within the material where it is not in direct contact with the tissue below, or just an electrically conducting material (such as a paste, gel, and/or fluid in contact with a current and/or voltage source) that is adjacent to or connected to the surface of the interface apparatus.

As depicted in FIG. 2, a second free electrode 15 is attached on the individual to be stimulated, at any location, such as within the mouth (also as an electric source). An electric field 14 is generated between the electrodes. A free standing mechanical source 16 (the mechanical source may be, for example, any acoustic source such as an ultrasound device) is applied to the scalp via the interface component 10 and provides concentrated acoustic energy 18, (i.e., mechanical field) to a focused region of neural tissue, affecting a smaller number of neurons 22 than affected by the electric field 14, by the mechanical field 18 altering the tissue electromagnetic characteristics relative to the applied electric field 14, and thereby generating the altered current 24. Both the electrode 12, and the material, inert and/or active, of the interface component 10 can be designed such that they are acoustically matched and/or coupled with the mechanical field 18 that transmits through them (for example, one could use the matching and/or coupling to limit the attenuation and/or modification (i.e., dispersion effects, phase shifting, beam focus, etc) of the mechanical field), and/or to alter the mechanical fields properties such as to be ideal for stimulation, for example through matching the acoustic impedances of the sources with the material of the bridging interface and/or the tissues. The interface could also have its electromagnetic properties matched and/or altered relative to the electrical source (and/or the tissues and/or the material of the interface bridging block) to facilitate the current alteration (such as by matching all of the electric impedances of the relevant parts through the appropriately designed interface). One could envision the interface component 10 could be filled with a fluid through which the mechanical field 18 can travel unimpeded where the electrode 12 is an electrically conducting thin latex like membrane (connected to a voltage or current source) that is coated in a conducting ultrasound gel. at the tissue-interface boundary through which the ultrasound energy can transmit. The fluid above the membrane could be non-conducting such as to prevent the spread of the electric field into the fluid (such that electrical energy focused towards the underlying tissue does not spread to the fluid above contained within the interface component). This concept of matching the properties may be applied in any permutation (via the interface and/or the tissues and/or with any potential sources, including the primary electrical source(s) and/or any means for altering the tissue electromagnetic properties (i.e., the ultrasound/mechanical field and/or source(s), chemical agent and/or source(s), thermal field and/or source(s), optical field/beam and/or source(s), and/or secondary electromagnetic field and/or source(s))).

Additionally, neither the electrode 12, nor the mechanical source need to be contained within the interface component, but for example in a situation where both are free standing, the interface component could be designed to couple the field(s) transmitted through it to the tissue below (through the appropriate acoustic and electric matching and/or coupling of the interface component and the tissues below (i.e., the mechanical and electrical source make contact with the interface mechanism at its boundary)). For example, the interface component 10, could be filled and/or coated with fluid(s) (such as degassed water) and/or gel(s) (such as ultrasound coupling gel) which in part serves to couple the mechanical/ultrasound source with the tissue and/or be fabricated of electrically conducting material which focuses an applied electrical field.

Additionally, the order in which the primary electrode 12 and mechanical source 16 are applied relative to the tissue and interface component 10 need not be fixed, the sources can be designed such that one field could transmit through the other source (or placed such that they do not interfere with each others' transmission (i.e., just through relative positioning), or even with a region of one removed so that the transmission path of the other is not crossed, in part or full, and/or such the mechanical and electrical field are generated from the same component). Additionally, the interlace component 10 can have ports that can be used to bring materials/fluids in and/or out (and/or on and/or off) of the interface apparatus 8 (such as for example with a cooling fluid, to circulate degassed water through the apparatus, an electrical conducting gel/fluid, etc).

Figure 3:
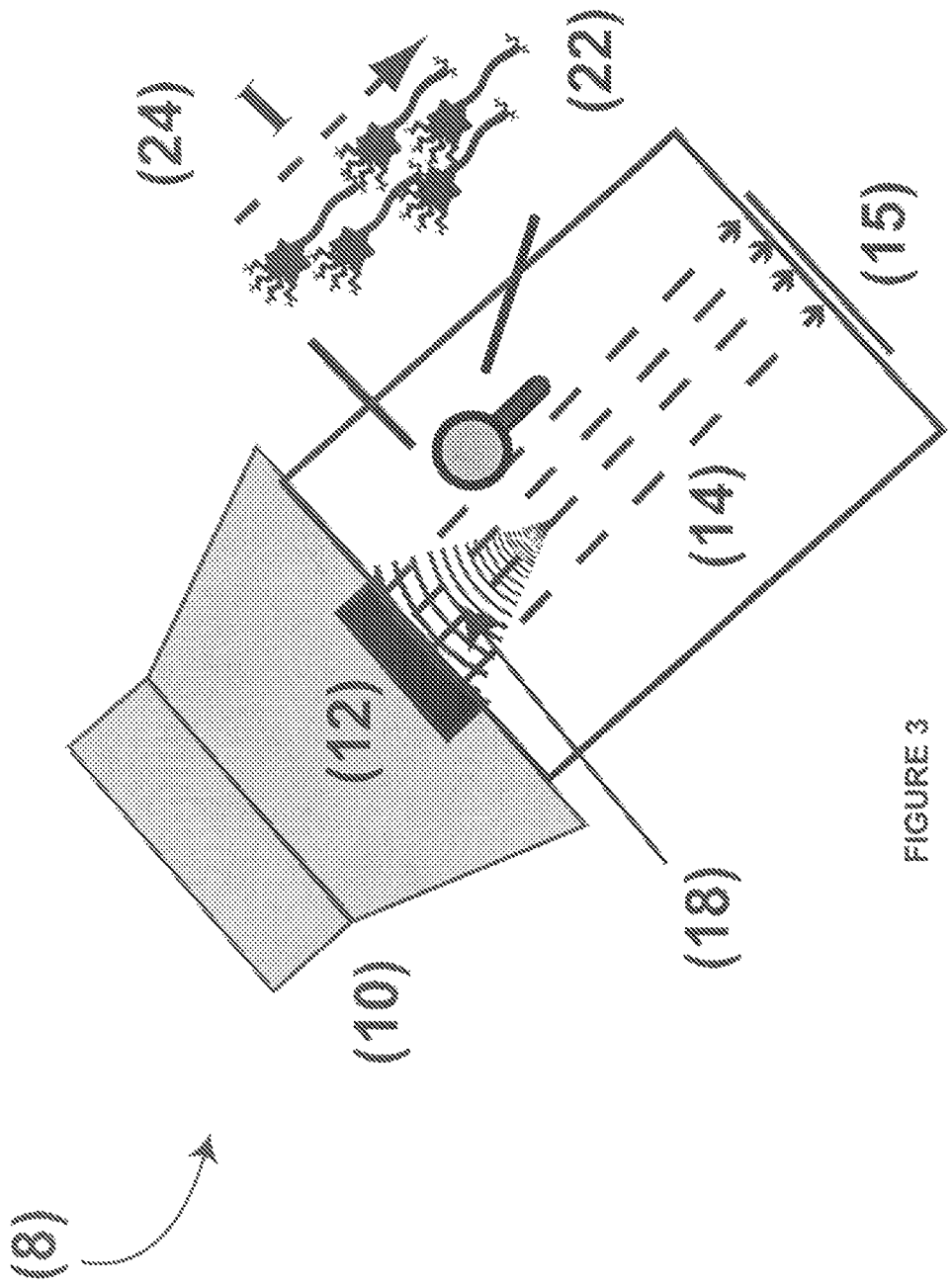
FIG. 3 is a plan view of an interface apparatus in accordance with the present disclosure.

FIG. 3, depicts another exemplary embodiment of the interface apparatus according to the present disclosure. The interface apparatus 8 illustrated in FIG. 3 may be applied to the area of neural stimulation. Interface component 10 can be a headpiece of a medical device between the sources and the tissue to be stimulated. An electrode 12 is applied to the tissue through the interface component 10. A second free electrode 15, also as an electric source, is attached on the tissue to be stimulated (or, at any location of proximal tissue); as with all the embodiments above, clearly a monopolar or multipolar electrode scheme is also possible. An electric field 14 is generated between the electrodes (or from a monopolar electrode where the second free electrode would not be used, or between multiple electrodes where a multipolar scheme is used). The same component that serves as an electrical source 12 can serve as the mechanical source (i.e., the mechanical source may be any acoustic source such as an ultrasound device, such that the ultrasound transducer face could also be composed of materials that could serve as the electric field source—such as for example placing the entire face of the transducer(s) at a voltage relative to the tissue) or the mechanical source could be a separate piece entirely, as in the previous figures. The electrical/mechanical source is applied to the tissue and provides concentrated acoustic energy 18, (i.e., mechanical field) to a focused region of neural tissue, affecting a smaller number of neurons 22 than affected by the electric field 14, by the mechanical field 18 altering the tissue electromagnetic characteristics relative to the applied electric field 14, and thereby generating the altered current 24. The apparatus can be connected to the underlying tissue(s) via fluids, gels, creams, pastes, and/or any appropriate material whereby the material may coat the entire apparatus, be at the apparatus-tissues(s) interface, be contained within the apparatus, and/or be injected into the path to the targeted area (from either an external material source and/or an integrated material chamber housed in the apparatus).

Another embodiment disclosed herein based on this principles elaborated on throughout could be a tDCS electrode cap which is similar to the above interface apparatus, with the means for altering the electromagnetic properties of the tissues to be stimulated removed. The electrodes could be placed for functional targeting based on a subject's specific condition or anatomy. It could also be based on dry electrodes, which would not leave debris from stimulation on the subject (or based on whatever means was acceptable for medically fixing the electrodes/or bridging the electrical fields to the individual's scalp and underlying tissues).

And furthermore, the interface component(s) in conjunction with the altered current generation could similarly be applied in the areas of altering cellular metabolism, physical therapy, drug delivery, and gene therapy as explained in the referenced patent application (U.S. patent application Ser. No. 11/764,468, Apparatus and Method for Stimulation of Biological Tissue) and above. These examples are provided not to be exhaustive, but as an example of potential applications.

As should be noted by one skilled in the art, throughout this entire disclosure, the reference to tissue can serve to mean tissue overlying the final stimulated tissue and all or some of the subsequent underlying or proximal tissue to be targeted for stimulation (i.e., where fields might be transmitted through multiple tissues before being focused on their final tissue focus—such as for example, through the skin, skull, CSF, gray matter, and white matter to be focused on underlying gray matter nuclei during stimulation of deep gray matter nuclei in the brain (i.e., tissue would refer to all of the tissues in the path of the stimulation field(s) and/or agents)). Further, the different sources (i.e., primary electrical source and means for altering the tissue electromagnetic properties) can be combined as single units. Additionally, the term material is not meant to be exclusive, but to refer to both active and/or inert materials throughout the document.

In accordance with the present disclosure, the embodiments disclosed herein may be used with a process that stimulates tissues through the combined application of electrical and mechanical fields (and/or chemical agents, thermal fields, optical fields/beams, and/or secondary electromagnetic fields) for the perturbation and/or modification of tissue permittivity and/or tissue conductivity for the generation of a new and/or altered displacement currents and/or ohmic currents, the generation of a new electric field with corresponding new ohmic and displacement current components (generated due to the tissue perturbation relative to the applied electric field), and/any currents that result due to continuity conditions with altered currents from the tissue electromagnetic property perturbation, and/or any combination thereof for stimulation.

While the inventions within this disclosure have been illustrated and described in detail in the drawings and/or foregoing description, the same is to be considered as illustrative and not restrictive in character, it being understood that embodiments have been shown and described and that all changes and modifications that come within the spirit of these inventions are desired to be protected.

What is claimed is:

1. A stimulation apparatus comprising:
   a wearable item configured to be worn on a head of a user;
   one or more stimulation sources coupled to the wearable item comprising one or more electrodes; and
   circuitry operably coupled to the wearable item and operably connected to the one or more stimulation sources, the circuitry being configured to receive a signal from a telecommunication device that activates use of the one or more stimulation sources to provide stimulations to the user and in response to receiving the signal, limit a number of times the one or more stimulation sources are used on the user or a number of stimulations that are provided to the user per session;
   wherein the wearable item further comprises at least one material that acts as a bridging medium and wherein the wearable item is configured such that when worn on the head of a user, at least one of the electrodes is positioned in an area around a scalp of the user.

2. The apparatus according to claim 1, wherein the one or more stimulation sources are embedded in the wearable item.

3. The apparatus according to claim 1, wherein the one or more stimulation sources are fastened to the wearable item.

4. The apparatus according to claim 1, wherein the material matches electromagnetic properties of the one or more stimulation sources with the tissue.

5. The apparatus according to claim 1, wherein the apparatus comprises multiple removable parts.

6. The apparatus according to claim 1, wherein the wearable item is a helmet.

7. The apparatus according to claim 1, wherein the wearable item is a wrap.

8. The apparatus according to claim 1, wherein the wearable item is adjustable.

9. The apparatus according to claim 1, wherein the material matches acoustic properties of the one or more stimulation sources with the tissue.

* * * * *